US005693624A

United States Patent [19]
Hardy et al.

[11] Patent Number: 5,693,624
[45] Date of Patent: Dec. 2, 1997

[54] STERILE GEL COMPOSITIONS FOR WOUND TREATMENT

[75] Inventors: Craig J. Hardy, Bridgemere; Charlotte Maria Findlay, Skipton, both of United Kingdom

[73] Assignee: Johnson & Johnson Medical, Inc., Arlington, Tex.

[21] Appl. No.: 462,243

[22] Filed: Jun. 5, 1995

[30] Foreign Application Priority Data

Jul. 18, 1994 [GB] United Kingdom ............ 9414454

[51] Int. Cl.$^6$ ............................................. A61K 31/715
[52] U.S. Cl. ........................... 514/54; 424/488; 424/443; 424/445; 514/944
[58] Field of Search ............ 514/54, 944; 536/3; 424/488, 407, 443, 445

[56] References Cited

U.S. PATENT DOCUMENTS

| | | | |
|---|---|---|---|
| 3,640,741 | 2/1972 | Etes | 424/32 |
| 4,391,799 | 7/1983 | Mason, Jr. et al. | 424/81 |
| 4,393,048 | 7/1983 | Mason et al. | 424/132 |
| 4,393,076 | 7/1983 | Noda et al. | 424/133 |
| 4,500,511 | 2/1985 | Kigasawa et al. | 424/81 |
| 4,525,348 | 6/1985 | Arizono et al. | 424/81 |
| 5,135,755 | 8/1992 | Czeck et al. | 424/445 |
| 5,336,501 | 8/1994 | Czech et al. | 424/488 |
| 5,416,205 | 5/1995 | della Valle et al. | 424/488 |
| 5,482,932 | 1/1996 | Thompson | 514/54 |
| 5,523,093 | 6/1996 | dela Valle et al. | 424/488 |

FOREIGN PATENT DOCUMENTS

| | | |
|---|---|---|
| 0 112 852 B1 | 7/1984 | European Pat. Off. . |
| 0 159 168 A2 | 10/1985 | European Pat. Off. . |
| 0 379 147 A2 | 7/1990 | European Pat. Off. . |
| 0 459 378 A1 | 4/1991 | European Pat. Off. . |
| 0 459 378 A1 | 12/1991 | European Pat. Off. . |
| 0 532 275 A1 | 3/1993 | European Pat. Off. . |
| 0 568 368 A1 | 3/1993 | European Pat. Off. . |
| 0 586 260 A1 | 9/1994 | European Pat. Off. . |
| 2 489 145 A2 | 5/1982 | France . |
| WO 8400111 | 1/1984 | WIPO . |

OTHER PUBLICATIONS

European Patent Standard Search Report for EP 95304958.2 dated Jan. 12, 1995, a corresponding foreign application.
European Patent Standard Search Report for GB 9414454.0 dated Oct. 17, 1994, a corresponding foreign application.
Search Report for Singapore Patent Application No. 9500880-1 dated Aug. 14, 1996, a corresponding foreign application.

*Primary Examiner*—James H. Reamer
*Attorney, Agent, or Firm*—Andrew C. Farmer

[57] ABSTRACT

The invention provides aqueous gel compositions for use as wound dressings and comprising from 2% to 10% w/v of alginate and from 25% to 40% w/v of polyhydric alcohol, said compositions being substantially sterile. The alginate is preferably sodium alginate and/or potassium alginate. the polyhydric alcohol is preferably propylene glycol or hexylene glycol. Also provided is a process of making such gel compositions comprising the steps of: providing an aqueous gel having the above composition and sterilizing the aqueous gel. Preferably, the aqueous gel is sterilized by heating.

17 Claims, No Drawings

STERILE GEL COMPOSITIONS FOR WOUND TREATMENT

The present invention relates to sterile gel compositions for application to the surface of wounds, such as decubitus ulcers and burns. The present invention also relates to a method of making such sterile gel compositions.

Aqueous gel compositions for application to the surface of wounds to assist healing are known. The purpose of applying the gels is to form a wound-friendly and humectant wound contact layer between the wound surface and conventional wound dressing layers. This also helps to reduce the adherence of conventional wound dressings, such as bandages or gauzes, to the wound surface. The aqueous gel can also serve as a vehicle for pharmaceutically active agents such as antiseptics or antibiotics.

U.S. Pat. No. 4,393,048 describes protective gel compositions for wounds comprising about 0.5 to 3% by weight alkali metal alginate, about 8 to 12% by weight glycerol and about 82 to 90% by weight water. Medicaments in an amount of 0.01 to 10% by weight may optionally be included in the compositions. The resulting gel is brushed over the surface of the wound and dries in air to form a non-toxic, flexible and stretchable film covering the wound.

A drawback of the gel compositions described in U.S. Pat. No. 4,393,048 is that they cannot readily be prepared in a sterile form suitable for medical applications. This is because the usual methods of sterilisation, namely gamma-ray irradiation or autoclaving, result in hydrolysis of the alginate and consequent drastic reduction in the gel viscosity. This rules out sterilisation of the alginate gel after it has been manufactured and filled into packages. In fact, the only way to manufacture an alginate gel of this type that is sterile would be to sterilise all the ingredients dry and then mix and package them under aseptic conditions. This method of manufacture would be prohibitively expensive for the wound dressings market.

WO84/00111 describes heat sterilisable pharmaceutical gel compositions for the treatment of burns, cuts, wounds or abrasions. The gel compositions comprise a pharmaceutically acceptable glycol and a cellulose derivative which is heat sterilizable. The preferred glycol is propylene glycol, preferably in an amount of 20–30% w/v. The preferred cellulose derivative is hydroxy ethyl cellulose, preferably in an amount of 1–4% w/v. The gel compositions optionally contain medicaments and/or dissolved physiologically acceptable salts. The use of hydroxy ethyl cellulose gives a gel that is heat sterilisable. That is to say, the gel retains its consistency and does not break down into a liquid when it is sterilised in an autoclave.

A drawback of the gel compositions described in WO84/00111 is that the heat sterilisable cellulose derivatives are inherently less effective in promoting wound healing than natural biopolymers such as alginates.

Accordingly, it is an object of the present invention to provide a heat sterilisable alginate gel for use in the treatment of burns, cuts, wounds, ulcers or abrasions.

The present invention provides an aqueous gel composition for use as a wound dressing comprising from 2% to 10% w/v of alginate and from 15% to 40% w/v of polyhydric alcohol, said composition being substantially sterile.

Surprisingly, it has been found that the inclusion of relatively large amounts of polyhydric alcohol (more than 15% w/v) results in an alginate gel that is stabilised against hydrolysis and consequent loss of viscosity during autoclave sterilisation. Sterilisation can be carried out by autoclaving using standard conditions. Compositions containing more than 40% w/v of polyhydric alcohol tend to separate on autoclaving. Such compositions can also cause discomfort or stinging when applied to a wound.

The alginate may consist of one or more of alginic acid and its salts. Preferably, the alginate consists of sodium alginate and/or potassium alginate. Preferably, the gel compositions comprise 3% to 6% w/v of the alginate. Preferably, the molecular weight of the alginate is in the range of 50,000 to 500,000.

The polyhydric alcohol preferably comprises one or more $C_3$–$C_6$ dihydric or trihydric alcohols, more preferably $C_3$–$C_6$ dihydric alcohols and most preferably propylene glycol or hexylene glycol. Other preferred polyhydric alcohols include ethylene glycol, butylene glycol, glycerol, diethylene glycol, dipropylene glycol, polyethylene glycol and polypropylene glycol. Preferably, the composition contains a total of 20% to 35% w/v of the one or more polyhydric alcohols.

The entire balance of the gel compositions other than the alginate and polyhydric alcohol may consist of water. However, preferably, the gel compositions also contain 0.01% to 10% w/v of one or more pharmaceutically active compounds, more preferably 0.1% to 5% w/v of such compounds. Preferred pharmaceutically active compounds are selected from: antiseptics such as chlorhexidine or silver sulphadiazine; antibiotics such as pencillins or tetracyclines; analgesics such as aspirin, paracetamol, ibuprofen or naproxen; steroids; glycosaminoglycans such as ihyaluronic acid and its salts, chondroitin sulfate or heparan sulfate; vitamins such as vitamins A and E; haemostats; cytokines; antibodies; enzymes; inflammatory agents; anti-inflammatory agents, and growth factors. Preferably, the total water content of the aqueous gel is from 55% to 79% w/v.

The aqueous gel preferably further comprises from 0.1% to 5% w/v of dissolved salts. The salts we preferably selected from the chlorides, iodides, sulfates, phosphates, bromides, carbonates, bicarbonates and hydroxides of sodium, potassium, ammonium, aluminum, zinc, silver and calcium. The dissolved salts preferably comprise sodium chloride, since it has been found that the presence of small amounts of sodium chloride can significantly affect the change in viscosity of the gel on sterilisation. The sodium chloride content thus provides a further parameter with which to control the viscosity of the sterile gel compositions. Also preferably, the gel compositions comprise phosphate salts or other suitable buffers to regulate the pH of the gel.

As noted above, an advantageous feature of the gels according to the present invention is that they retain useful viscosity after sterilisation. This allows the gels to be coated onto the wound site reasonably conveniently.

The present invention also provides a process to prepare a substantially sterile gel for application to burns, cuts, wounds, ulcers or grazes, the process comprising the steps of: providing an aqueous gel comprising from 2% to 10% w/v of alginate and from 15% to 40% w/v of polyhydric alcohol; and heat sterilizing the aqueous gel.

Preferred compositions and constituents of the aqueous gel are the same as those described above for the gel compositions according to the present invention.

Preferably, the step of sterilizing is carried out by heating at a temperature for a period sufficient to give a sterility measure of $FO_4$, more preferably $FO_8$, and most preferably $FO_{12}$. Preferably, this step of heat-sterilising is carried out under pressure in an autoclave.

Preferably, the process according to the present invention further comprises the step of inserting the aqueous gel into a package prior to carrying out the step of sterilising. Preferably, the package is a tube, can or sachet. This procedure is advantageous because it enables the aqueous gels to be made under non-sterile conditions, packaged and then sterilised, thereby providing a relatively low-cost route to packaged sterile alginate gels.

In order for the aqueous gel to be easily packaged prior to sterilisation, it is preferable for the viscosity of the aqueous gel before sterilisation to be less than 150,000 cps, preferably less than 100,000 cps.

Specific embodiments of the gel compositions and processes according to the present invention will now be described further in and by the following Examples:

EXAMPLE 1

The effect of propylene glycol (PG) content on the heat sterilisability of aqueous alginate gels is determined as follows.

A number of aqueous alginate gels is made up according to the following proportions. The sodium alginate (Protanal LF 10/60) has a stated molecular weight in the range 70,000 to 200,000. The potassium alginate has a molecular weight range of 300,000 to 350,000. Each gel is then sterilised in an autoclave to give a sterility measure of $FO_{12}$.

The viscosity in centipoise (cps) at 20° C. is measured before and after sterilisation for each of the gels. The viscosity measurements are carried out with a rotating spindle, dial reading mechanical viscometer manufactured by Brookfield Viscometers Ltd. Brookfield Spindle No. 7 is used at a speed of 10 revolutions per minute. The sample is held in a cylindrical container measuring at least 50 mm in diameter and holding sample to a depth of at least 70 mm.

The results are as follows (, denotes a comparative example).

| PG Conc. % w/v | Unsterile Viscosity (cps) | Sterile Viscosity (cps) |
|---|---|---|
| a) 4% w/v Sodium Alginate | | |
| 5* | 2000 | 100 |
| 10* | 2200 | 100 |
| 15 | 4300 | 130 |
| 20 | 9000 | 190 |
| 25 | 7480 | 270 |
| 30 | 2700 | 13600 |
| 35 | 200 | 30000 |
| 40 | 50 | 17600 |
| b) 5% w/v Sodium Alginate | | |
| 5* | 4000 | 200 |
| 10* | 6000 | 220 |
| 15 | 12300 | 320 |
| 20 | 19800 | 490 |
| 25 | 16200 | 21400 |
| 30 | 5780 | 53000 |
| 35 | 1400 | 34000 |
| 40 | 50 | Separated |
| c) 6% w/v Sodium Alginate | | |
| 5* | 7200 | 440 |
| 10* | 17600 | 460 |
| 15 | 29920 | 740 |
| 20 | 38000 | 2200 |
| 25 | 28000 | 27000 |
| 30 | 10600 | 104000 |
| 35 | 4000 | 139000 |
| 40 | 70 | Separated |
| d) 3% w/v Potassium Alginate | | |
| 5* | 8400 | 180 |

-continued

| PG Conc. % w/v | Unsterile Viscosity (cps) | Sterile Viscosity (cps) |
|---|---|---|
| 10* | 12000 | 190 |
| 15 | 14000 | 400 |
| 20 | 24200 | 440 |
| 25 | 30200 | 700 |
| 30 | 44000 | 1100 |
| 35 | 35200 | 1760 |
| 40 | 12400 | 30000 |
| e) 4% w/v Potassium Alginate | | |
| 5* | 33000 | 900 |
| 10* | 32000 | 1200 |
| 15 | 42600 | 1700 |
| 20 | 61200 | 1940 |
| 25 | 78000 | 3460 |
| 30 | 87200 | 4100 |
| 35 | 67200 | 30000 |
| 40 | 28000 | 122000 |
| f) 5% w/v Potassium Alginate | | |
| 20 | 141000 | 5400 |
| 25 | 129000 | 7600 |
| 30 | 154000 | 36400 |
| 35 | 114000 | 172000 |
| 40 | 26400 | 126000 |

These results demonstrate clearly that, by selecting the level of alginate and propylene glycol, it is possible to produce an alginate gel which maintains, or even increases, its viscosity on autoclaving.

EXAMPLE 2

The procedure of Example 1 is followed for the following compositions, in which the propylene glycol (PG) of Example 1 has been replaced by hexylene glycol (HG). The results are as follows (* denotes a comparative example).

| HG Conc. % w/v | Unsterile Viscosity (cps) | Sterile Viscosity (cps) |
|---|---|---|
| a) 3% w/v Sodium Alginate | | |
| 5* | 400 | 4 |
| 10* | 980 | 14 |
| 15 | 2900 | 40 |
| 20 | 1200 | 60 |
| 25 | 80 | 10000 |
| 30 | 20 | Separated |
| b) 4% w/v Sodium Alginate | | |
| 5* | 2200 | 50 |
| 10* | 4400 | 104 |
| 15 | 9700 | 156 |
| 20 | 2900 | 2100 |
| 25 | 25 | 10000 |
| 30 | 10 | Separated |
| c) 5% w/v Sodium Alginate | | |
| 5* | 4980 | 190 |
| 10* | 14200 | 236 |
| 15 | 17400 | 360 |
| 20 | 6600 | 32000 |
| 25 | 300 | 20600 |
| 30 | 20 | Separated |
| d) 6% w/v Sodium Alginate | | |
| 5* | 9850 | 100 |
| 10* | 28700 | 100 |
| 15 | 30300 | 24400 |
| 20 | 13400 | 39600 |

-continued

| HG Conc. % w/v | Unsterile Viscosity (cps) | Sterile Viscosity (cps) |
|---|---|---|
| 25 | 1000 | 780000 |
| 30 | Separated | Separated |

These results demonstrate that hexylene glycol can also be used to form autoclave-stable alginate gels. It appears that less hexylene glycol than propylene glycol is needed to achieve equivalent stabilisation.

EXAMPLE 3

The effect of adding 0.6% w/v of sodium chloride to a 3% sodium alginate gel is illustrated by the following data (* denotes a comparative example)@

| PG Conc. % w/v | Unsterile Viscosity (cps) | Sterile Viscosity (cps) |
|---|---|---|
| 2.5* | 1000 | 105 |
| 5.0* | 1100 | 145 |
| 10.0* | 4010 | 135 |
| 15.0 | 2950 | 170 |
| 20.0 | 584 | 2000 |
| 25.0 | 44 | 12000 |
| 40.0 | 13 | 260 |

It can be seen that the addition of 0.6% w/v sodium chloride to the aqueous alginate gel at 25% w/v PG content results in a gel having satisfactory viscosity after autoclaving.

The above embodiments have been described by way of example only. Many other embodiments falling within the scope of the accompanying claims will be apparent to the skilled reader.

We claim:

1. An aqueous gel composition for use as a wound dressing comprising from 2% to 10% w/v of a water-soluble alginate salt and from 1% to 40% w/v of a $C_3$–$C_6$ dihydric or trihydric alcohol, said composition being substantially sterile and having been sterilized by heat sterilization.

2. An aqueous gel composition according to claim 1, wherein the composition comprises from 3% to 6% w/v of the alginate salt.

3. An aqueous gel composition according to claim 1, wherein the composition contains 20% to 35% w/v of the $C_3$–$C_6$ dihydric or trihydric alcohol.

4. An aqueous gel according to claim 3, wherein the $C_3$–$C_6$ dihydric alcohol is selected from the group consisting of propylene glycol and hexylene glycol.

5. An aqueous gel according to claim 1, wherein the water content is from 55% to 83% w/v.

6. An aqueous gel according to claim 1, further comprising from 0.01% to 10% w/v of pharmaceutically active compounds.

7. An aqueous gel according to claim 6 comprising from 0.1% to 5% w/v of the pharmaceutically active compounds.

8. An aqueous gel according to claim 6, wherein the pharmaceutically active compounds comprise an antiseptic, an antibiotic, an analgesic, a glycosaminoglycan, a vitamin, an antibody, an enzyme, a haemostat, a cytokine, an inflammatory agent, an anti-inflammatory agent, a steroid or a growth factor.

9. An aqueous gel according to claim 1 and further comprising from 0.1% to 5% w/v of dissolved salts.

10. An aqueous gel according to claim 9, wherein the dissolved salts comprise sodium chloride or phosphate salts.

11. A process to prepare a substantially sterile gel for use as a wound dressing, the process comprising the steps of:

providing an aqueous gel comprising from 2% to 10% w/v of a water-soluble alginate salt and from 15% to 40% w/v of a $C_3$–$C_6$ dihydric or trihydric alcohol; and heat sterilizing the aqueous gel.

12. A process according to claim 11, wherein the step of sterilizing is carried out by heating at a temperature and for a time sufficient to give a sterility measure of $FO_4$.

13. A process according to claim 12, wherein the step of heat-sterilizing is carried out under pressure in an autoclave.

14. A process according to claim 11, wherein the alginate comprises sodium alginate or potassium alginate.

15. A process according to claim 11 and further comprising the step of inserting the aqueous gel into a package prior to the step of sterilization.

16. A process according to claim 15, wherein the package is a tube, can or sachet.

17. A process according to claim 11 wherein the polyhydric alcohol comprises propylene glycol or hexylene glycol.

* * * * *